(12) United States Patent
Melson et al.

(10) Patent No.: US 7,462,479 B2
(45) Date of Patent: *Dec. 9, 2008

(54) INFECTIOUS BRONCHITIS VIRUS VACCINE

(75) Inventors: Lillian Melson, Millsboro, DE (US);
Faris F. Jirjis, Omaha, NE (US)

(73) Assignee: Intervet International B.V., Boxmeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/865,957

(22) Filed: Oct. 2, 2007

(65) Prior Publication Data

US 2008/0026449 A1    Jan. 31, 2008

Related U.S. Application Data

(63) Continuation of application No. 10/848,589, filed on May 17, 2004, now Pat. No. 7,291,342.

(60) Provisional application No. 60/471,796, filed on May 19, 2003.

(51) Int. Cl.
*C12N 7/00* (2006.01)

(52) U.S. Cl. .................................. 435/235.1

(58) Field of Classification Search ........................ None
See application file for complete search history.

(56) References Cited

U.S. PATENT DOCUMENTS

| | | | |
|---|---|---|---|
| 4,751,079 A | 6/1988 | Burger | |
| 6,086,892 A | 7/2000 | Cook | |
| 7,291,342 B2 | 11/2007 | Melson et al. | |
| 2004/0265339 A1 | 12/2004 | Melson et al. | |

OTHER PUBLICATIONS

Jackwood, Mark W. et al., "Attenuation, Safety, and Efficacy of an Infectious Bronchitis Virus GA98 Serotype Vaccine" Jul. 2003, Avian Diseases. 47:627-632.
Lee, Chang-Won, et al., "Origin and evolution of Georgia 98 (GA98), a new serotype of avian infectious bronchitis virus" (2001), Virus Research. 80:33-39.
Lee, Chang-Won, et al., "Identification and Analysis of the Georgia 98 Serotype, a New Serotype of Infectious Bronchitis Virus" (2001), Avian Diseases. 45:164-172.
Jia, Wei, et al., "Immunogenicity and Safety of an Attenuated Georgia Type Infectious Bronchitis Vaccine", (2005) 54th Western Poultry Disease Conference (3 pages).
Otsuki, et al. "Studies on avian infectious bronchitis virus (IBV). I. Resistance of IBV to chemical and physical treatments." Archives of Virology. 1979; 60(1):25-32, Abstract only.
The Poultry Informed Professional, published by the Department of Avian Medicine of the University of Georgia College of Veterinary Medicine, Issue 37, May 2000.

*Primary Examiner*—Bruce Campell
*Assistant Examiner*—Nicole Kinsey White
(74) *Attorney, Agent, or Firm*—Aaron L. Schwartz

(57) ABSTRACT

Embodiments of the present invention generally relate to a novel attenuated infectious bronchitis virus (IBV) of GA-98 isolate. Further, other embodiments of the present invention generally relate to methods of immunizing avian against an infectious bronchitis virus. As well, further embodiments relate to method of making a vaccine and/or immunogenic composition for protecting avian, such as poultry, from an infectious bronchitis virus of strain GA-98.

1 Claim, No Drawings

INFECTIOUS BRONCHITIS VIRUS VACCINE

CROSS REFERENCE TO RELATED APPLICATION

This application is a continuation of U.S. application Ser. No. 10/848,589, filed on May 17, 2004 (now U.S. Pat. No. 7,291,342), which claims the benefit under 35 U.S.C. § 119 (e) of U.S. Provisional Application No. 60/471,796, filed May 19, 2003.

FIELD OF THE INVENTION

The present invention relates to a new infectious bronchitis virus vaccine(s) for use in immunizing avian species and methods for its use.

BACKGROUND OF THE INVENTION

Infectious bronchitis virus (IBV) is a member of the genus coronavirus of the family Coronaviridae. The virus is usually about 80-100 nm in size, being round with projecting 20 nm spikes. IBV is the causative agent of an acute, highly contagious disease in chickens of all ages, affecting the respiratory, reproductive and renal systems.

IBV has been reported in all countries where an intensive poultry industry has been developed. Young chickens up to 4 weeks of age are most susceptible to respiratory disease, infection leading to high rates of morbidity and to mortality resulting from secondary bacterial infection. Infection in layers results in a drop in egg production, or failure to lay at full potential, together with an increase in the number of downgraded eggs with thin, misshapen, rough and soft-shells produced. Although layers usually recover from the disease, their egg production rarely returns to pre-infection levels. Thus infection of flocks of chickens with IBV can have a serious economic effect.

Spackman and Cameron (Veterinary Record, (1983), 113, 354-355) isolated IBV from pheasants with a history of respiratory signs and aberrant egg production. This disease problem in pheasants was successfully controlled by the use of oil-based inactivated IBV vaccine. Thus the term poultry, as used herein, is intended to embrace chickens, pheasants and any other domesticated bird serving as a source of eggs or meat and that are susceptible to infection by IBV.

The only practical means of preventing infectious bronchitis in poultry is to vaccinate against the infection. Two main types of vaccine are available and they are attenuated and inactivated.

One such known isolate is the Georgia 98 strain (GA-98), which was received from the University of Georgia Poultry Diagnostic and Research Center (PDRC) by Intervet, Inc., Millsboro, Del., U.S. Veterinary License No. 286 on Feb. 11, 2000. This strain has shown resilience to many of the commercially available IBV vaccines. Accordingly, the art field is in search of a vaccine for the GA-98 strain of IBV.

SUMMARY OF THE INVENTION

Various embodiments of the present invention generally relate to a vaccine and/or vaccine composition comprising GA-98, in a live (naturally occurring low pathogenic), attenuated and/or inactivated form.

An exemplary, non-limiting, embodiment of the present invention is deposited at the American Tissue Culture Collection. 10801 University Blvd. Manassas, Va, 20110-2209 USA, under accession no. PTA-4820, deposited on November 26, 2002. The deposit is also identified as "Infectious Bronchitis Virus: IBV GA 98 MS P41 110800."

Further embodiments of the present invention generally relate to methods of vaccinating birds, such as poultry.

DETAILED DESCRIPTION OF THE INVENTION

The novel vaccine strain of the present invention was made from GA-98 strain, and is deposited at the American Tissue Culture Collection, under accession no. PTA-4820, deposited on Nov. 26, 2002. Such strain was received from University of Georgia Poultry Diagnostic and Research Center (PDRC) by Intervet Inc., Millsboro Del., U.S. Veterinary License No. 286 on Feb. 11, 2000. Since receipt, the virus has been passed in specific pathogen free (SPF) chicken embryos and heat treated to facilitate attenuation.

Accordingly, in an embodiment the present invention is an infectious bronchitis vaccine for use in immunizing poultry comprising an immunogenically effective amount of attenuated strain Georgia 98 (GA-98), a sample of which is deposited at the American Tissue Culture Collection, under accession no. PTA-4820, and a pharmaceutically acceptable carrier or diluent. In certain embodiments, a stabilizer is also present, such as Stabilizer No. 1. The strain may be live, attenuated, or inactivated.

Other embodiments of the present invention may utilize further and/or other methods of attenuation. For example, and not by way of limitation, an attenuated IBV is obtainable by passaging the IBV in a culture on a suitable medium a sufficient number of times to reduce its pathogenicity whilst retaining its immunogenicity. Preferably the IBV is passaged at least 20 times.

A specific medium common for attenuation is an embryonated egg. Inoculation of the eggs can be via the allantoic cavity, chorioallantoic membrane, yolk sac, amniotic cavity or even direct into the embryo. The virus can be passaged at regular intervals of from 7 hours up to 4 days. Commonly, passaging takes place between 16 to 36 hours, preferably every 24 hours.

Alternatively, attenuation may also be achieved by passaging the virus in avian cell culture, such as chick embryo kidney cells.

In an embodiment, the present invention is a process for the preparation of live infectious bronchitis vaccine from an IBV strain comprising the steps of passaging the IBV strain in a culture on a suitable medium for sufficient number of times to reduce its pathogenicity while retaining its immunogenicity, heat treating the passaged culture, harvesting the attenuated virus and processing the harvested material to produce a vaccine strain of IBV, wherein the IBV is of the same serotype as that of IBV strain GA-98 deposited at the American Tissue Culture Collection, under accession no. PTA-4820. Further embodiments comprise heating the virus in a water bath. In yet other embodiments, there are at least one step of heat treating the virus.

In another embodiment, a method of producing a vaccine comprising a GA-98 strain comprising the steps of:

inoculating a suitable substrate with the GA-98 virus strain;

growing the strain on the substrate;

harvesting the virus;

optionally attenuating the virus if the virus is not non-pathogenic; and, formulating a vaccine from the virus.

In various embodiments, the substrate is a substrate selected from a specific pathogen free egg (SPF eggs), a mammalian cell, and an avian cell. In various further embodiments, a pharmaceutically acceptable carrier or diluent is formulated with the vaccine virus strain. As well, any method of attenuation may be used, as is common in the art, such as passaging the virus strain and heat treating the virus strain.

After the virus is attenuated, the virus may be stored until use. In an embodiment, the virus is lyophilized. The lyophilized virus may then be rehydrated for use. In another embodiment, the virus is frozen.

In further embodiments, the deposited attenuated strain may be used in the preparation of a live vaccine. Thus according to a further embodiment of the present invention there is provided a live infectious bronchitis vaccine for use in immunizing poultry, said vaccine derived from the IBV described above, the GA-98 strain.

According to another embodiment of the invention there is provided a process for the preparation of a live infectious bronchitis vaccine which comprises passaging the GA-98 serotype, or strain as hereinbefore described, in a culture on a suitable medium a sufficient number of times to reduce its pathogenicity whilst retaining its immunogenicity and processing the material harvested to produce a vaccine. Preferably the virus is passaged at least five (5) times.

The present invention also relates to the use of an attenuated GA-98 strain, as hereinbefore described for use in vaccinating poultry against IBV.

Such attenuated vaccines may be administered by eye drop, nose drop, in drinking water, or by spraying the birds, at any age from one day old up to point of lay (about 18 weeks). The dosage used is preferably in the range of log $10^{3.0}$ to log $10^{7.0}$ EID$_{50}$ per bird, preferably between log $10^{4.0}$ and log $10^{5.0}$ EID$_{50}$ per bird.

Such an attenuated IBV vaccine may be administered in combination with other live avian vaccines, for example Newcastle Disease Virus (NDV), Mareks Disease Virus (MDV), Infectious Bursal Disease (IBD), reovirus, Avian Encephalomyelitis, Chicken Anaemia Agent (CAA) and other IBV serotypes.

Alternatively, the novel IBV vaccine according to the invention may be presented as an inactivated vaccine. According to yet a further embodiment of the invention there is provided an inactivated infectious bronchitis vaccine for use in immunizing poultry, which vaccine comprises IBV which is derived from the GA-98 serotype described above.

For both live and inactivated vaccine production the IBV is usually grown in embryonated specific pathogen free (SPF) chicken eggs. However, the particular medium/substrate upon which the strain is grown is not substantially important to the invention. After harvesting, the virus may be inactivated, for use in a killed vaccine, using for example formaldehyde or beta-propiolactone. Other embodiments of acceptable substrates include, but are not limited to, mammalian cell lines, avian cell lines, and the like.

After inactivation and, if necessary, adjusting of the pH and neutralising of the inactivating agent, the inactivated virus may be mixed with an adjuvant. The adjuvant can be aluminium hydroxide or a composition consisting of mineral oil (e.g. Marcol 82) or a plant oil and one or more emulsifiers like Tween 80 and Span 80.

Inactivated vaccines are usually administered by subcutaneous or intramuscular injection at between 10 to 20 weeks of age. Inactivated vaccine may contain the antigenic equivalent of log $10^{5.0}$ to log $10^{8.0}$ EID$_{50}$ per bird dose, preferably log $10^{6.0}$ to log $10^{8.0}$ EID$_{50}$.

Such an inactivated IBV vaccine may be administered in combination with other inactivated avian vaccines, for example NDV, CAA, Egg Drop Syndrome 1976 and other IBV serotypes.

According to yet a further embodiment of the invention there is provided a method for protecting poultry against IBV comprising administering a vaccine as hereinbefore described to susceptible birds.

While the invention has been described in connection with specific embodiments, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended Claims are intended to cover such differences. Furthermore, all patents, patent applications, articles, and other publications mentioned herein are hereby incorporated by reference.

For a further understanding of various embodiments of the present invention, reference should be had to the following examples:

EXAMPLE

Materials and Methods
A. Animals
   Fifty-five (55) one-day-old specific pathogen free (SPF) Leghorn chickens were used. Chicks were hatched at Intervet from eggs obtained from Charles River/SPAFAS.
B. Vaccine Virus Preparation—GA 98 Attenuation
C. Vaccination
   On day of vaccination, one-day-old chicks were wing tagged and separated into two groups. Group 1 comprised 35 chicks and Group 2 comprised 20 chicks. Group 1 was vaccinated by coarse spray with the banked 1:100 dilution of IBV GA-98 vaccine. Vaccine was administered using the Intervet Model 850-1 Spray Cabinet, which delivers 0.07 ml of vaccine per dose.
   Group 2 was held as non-vaccinated controls.

TABLE 1

Experimental Groups in Efficacy Trial of Embodiment of the present invention

| Group | Number of Chicks | Vaccine | Estimated Vaccine Dose |
|---|---|---|---|
| 1 | 35 | Banked 1:100 dilution of IBV GA-98 | $10^3$ EID$_{50}$ per 0.07 ml dose |
| 2 | 20 | None | NA |

E. Housing
   Groups were placed in separate negative pressure isolator units, where they were held for the duration of the experiment.
F. Challenge
   1. Twenty-eight (28) days after vaccination, all chickens were challenged with IBV GA-98 challenge virus. Challenge virus was derived from IBV isolate GA/0470/98. Challenge virus was produced by passing the GA/0470/98 virus three times in SPF chicken embryos, harvesting allantoic fluid from the third embryo passage, mixing it with a stabilizer, and freezing at or below −65° C.

2. An aliquot of challenge virus was diluted 1:700 in tryptose phosphate broth (TPB) on day of challenge to yield $10^4$ $EID_{50}$ per ml.
3. Each chicken was inoculated with diluted challenge virus by administering one drop in each eye (0.06 ml total).
4. Diluted challenge virus was titrated in duplicate on day of challenge to confirm that the concentration was at least $10^4$ $EID_{50}$ per ml.

G. Evaluation of Protection

1. Protection was defined as failure to re-isolate IBV from the trachea after challenge. Five days after challenge, all chickens were euthanized and swabbed in the trachea. Each swab was placed in a tube containing 3 ml TPB and 1.5 mg/ml gentamicin. Tubes were vortexed and held at or below −65° C. until inoculation into eggs.
2. For each tracheal swab, six 11-day-old SPF embryonated chicken eggs were inoculated in the allantoic cavity with 0.2 ml of sample. Eggs were incubated at 37° C. with hourly turning.
3. Three days after inoculation, eggs were candled and dead embryos were discarded. Seven days after inoculation, all remaining embryos were examined for lesions typical of IBV infection, including stunting and curling, clubbed down, kidney urates, or death during the 4-7 day post-inoculation period.
4. To be an experimentally valid test, at least about 4 of the 6 inoculated embryos must be alive at the three day candling. If fewer than 4 embryos survived, tracheal swab fluid from that sample was filtered through a 0.45 μm ACRODISC low protein binding syringe filter to remove contaminating bacteria, and 0.2 ml filtrate was inoculated into each of six 11-day-old eggs as a retest.
5. Retests were also conducted on samples if an embryo died on days 4 through 7 post-inoculation, but showed no lesions typical of IBV, or if an embryo appeared slightly smaller than usual. These samples were not filtered before egg inoculation.

Results

A. Titrations

1. The GMT of titers conducted on the banking samples was $10^{2.78}$ $EID_{50}$/dose.
2. The GMT of backtiters conducted on the IBV GA-98 challenge virus was $10^{3.3}$ $EID_{50}$/dose.

B. Virus Re-Isolation

A summary of virus recovery results is shown in Table 2. Individual bird records are shown in Tables 3-7.

1. Non-vaccinated, Challenged Chickens
   Individual swab results are shown in Table 3.
   All 20 tracheal swabs from the non-vaccinated, challenged control chickens were positive for IBV recovery.

C. Vaccinated, Challenged Chickens a. Of 35 tracheal swab samples, 3 were positive for IBV recovery and 32 were negative, resulting in 91% protection. Virus recovery records are summarized in Table 4.
b. Six of the 35 samples had to be retested because fewer than the required 4 of 6 eggs inoculated per sample survived 3 days after inoculation. These 6 tracheal swab samples (#104, 105, 110, 115, 116, 118) were filtered through individual 0.45 μm low protein binding ACRODISC syringe filters to remove contaminating bacteria, and inoculated into eggs as described above All samples were negative for virus recovery. Virus recovery records are included in Table 5.
c. As controls for the filtered samples, 3 tracheal swab samples (#195, 200, 214) from the positive controls (non-vaccinated, challenged chickens) were filtered and retested by the same method. All were positive for virus recovery, demonstrating that IBV was recoverable after filtering samples for bacterial contamination. Records are included in Table 6.
d. Several embryos from eggs inoculated with 5 of the 35 samples died and showed structural abnormalities that are not typical of IBV infection (#95, 96, 103, 107, 119). These deformities included absence of head, eyes or feet, and failure of the abdominal wall to close.
e. Three additional tracheal swab samples from vaccinates were retested: a sample that was positive for IBV recovery (#90), and a sample that was negative (#124), and a sample that resulted in six normal embryos, one of which was small (#100). In the retests, sample 90 was again positive for IBV lesions, and samples 100 and 124 were again negative. These results are also included in Table 7.

IV. CONCLUSION

The challenge met 9CFR criteria, since the titer of the challenge virus was $\geq 10^{4.0}$ $EID_{50}$ per ml, and 0% of non-vaccinated chickens were protected against challenge.

IBV-GA-98 P46 vaccine administered by coarse spray at a dose of $10^{2.78}$ $EID_{50}$ per chicken provided 91% protection against IBV-GA-98 challenge. This establishes $10^{2.78}$ $EID_{50}$ per dose as the minimal protective dose for the IBV GA-98 vaccine.

Brief Description Of Tables

Table 2: Summary of virus recovery results

TABLE 3: VIRUS RECOVERY RECORDS OF NON-VACCINATED CONTROLS

TABLE 4: VIRUS RECOVERY RECORDS OF VACCINATES

TABLE 5: VIRUS RECOVERY RECORDS OF VACCINATES (RETESTED SAMPLES)

TABLE 6: VIRUS RECOVERY RECORDS OF NON-VACCINATES (RETESTED SAMPLES)

TABLE 7: VIRUS RECOVERY RECORDS FOLLOWING CHALLENGE OF VACCINATES (RETESTED SAMPLES)

TABLE 2

Percent Protection against IBV-GA-98 Challenge following Coarse Spray Vaccination of One-Day Old Chicks with IBV GA-98 P46

| Group | No. of Chickens Positive for IBV Recovery/Total Chickens | Percent Protection |
| --- | --- | --- |
| Vaccinates | 3/35 | 91% |
| Non-vaccinates | 20/20 | 0% |

TABLE 3

VIRUS RECOVERY RESULTS FROM NON-VACCINATED CONTROLS

| Sample # | # Eggs discarded day 3 post inoculation | # Positive/ # Total | IBV Recovery Outcome |
|---|---|---|---|
| 195 | 0 | 5/6 | Positive |
| 196 | 0 | 5/6 | Positive |
| 197 | 2 | 3/4 | Positive |
| 198 | 0 | 5/6 | Positive |
| 199 | 0 | 4/6 1 dead | Positive |
| 200 | 1 | 2/5 | Positive |
| 201 | 0 | 6/6 | Positive |
| 202 | 0 | 6/6 | Positive |
| 203 | 1 | 5/5 | Positive |
| 204 | 0 | 6/6 | Positive |
| 205 | 0 | /6 | Positive |
| 206 | 1 | 5/5 | Positive |
| 207 | 0 | 3/6 1 dead | Positive |
| 208 | 1 | 3/5 | Positive |
| 209 | 0 | 4/6 | Positive |
| 210 | 0 | 4/6 | Positive |
| 211 | 0 | 4/6 | Positive |
| 212 | 1 | 5/5 | Positive |
| 213 | 0 | 5/6 | Positive |
| 214 | 0 | 4/6 | Positive |
| Uninoculated Eggs | 0 | 0/7 1 dead | Negative Dead embryo appears normal |

TABLE 4

VIRUS RECOVERY RESULTS FROM VACCINATES

| Sample # | #Eggs dead day 3 P.I. | # Positive/ # Total | Comments | IBV Recovery Outcome | IBV Recovery Retest |
|---|---|---|---|---|---|
| 90 | 0 | 4/6 | | Positive | Positive |
| 91 | 0 | 0/6 | | Negative | |
| 92 | 1 | 0/5 | | Negative | |
| 93 | 2 | 0/4 | | Negative | |
| 94 | 0 | 0/6 | | Negative | |
| 95 | 0 | 0/6; 1 dead | Dead is deformed** | Inconclusive | Negative |
| 96 | 1 | 0/5 | 1 deformed** | Negative | Negative |
| 97 | 1 | 0/5 | | Negative | |
| 98 | 1 | 0/5 | | Negative | |
| 99 | 1 | 0/5 | | Negative | |
| 100 | 0 | 0/6 | 1 small | Negative | Negative |
| 101 | 0 | 0/6 | | Negative | |
| 102 | 2 | 0/4 | | Negative | |
| 103 | 0 | 0/6; 1 dead | Dead is deformed** | Inconclusive | Negative |
| 104* | 3 | 0/3 | Fewer than 4 embryos | Inconclusive | Negative |
| 105* | 4 | 0/2 | Fewer than 4 embryos | Inconclusive | Negative |
| 106 | 0 | 0/6 | | Negative | |
| 107 | 0 | 0/6; 1 dead | Dead is deformed** | Inconclusive | Positive |
| 108 | 2 | 0/4 | | Negative | |
| 109 | 2 | 0/4 | | Negative | |
| 110* | 3 | 0/3 | Fewer than 4 embryos | Inconclusive | Negative |
| 111 | 1 | 0/5 | | Negative | |
| 112 | 0 | 0/6 | | Negative | |
| 113 | 0 | 0/6 | | Negative | |
| 114 | 1 | 0/5 | | Negative | |
| 115* | 3 | 0/3; 2 dead | Fewer than 4 embryos Deaths recorded on day 7 appear to be early deaths | Inconclusive | Negative |
| 116* | 3 | 0/3 | Fewer than 4 embryos | Inconclusive | Negative |
| 117 | 2 | 0/4 | | Negative | |
| 118* | 3 | 0/3 | Fewer than 4 embryos | Inconclusive | Negative |
| 119 | 0 | 0/6; 2 dead | 1 dead is deformed** | Inconclusive | Positive |
| 120 | 0 | 0/6 | | Negative | |
| 121 | 1 | 0/5 | | Negative | |
| 122 | 1 | 0/5 | | Negative | |
| 123 | 1 | 0/5 | | Negative | |
| 124 | 0 | 0/6 | | Negative | Negative |

*Because of egg death within 3 days, these samples were filtered and retested; see Table 4 for retests.
**Deformities included no head, no feet, no eyes, open abdomen. These deformities are not lesions typical of IBV infection; see Table 6 for retests.

TABLE 5

VIRUS RECOVERY RECORDS OF VACCINATES: RETESTED SAMPLES

These samples were retested because fewer than 4 eggs survived 3 days after inoculation. Samples were filtered though 0.45 μm filters to eliminate bacteria before being inoculated into eggs.

| Sample # | # Eggs discarded 3 days post inoculation | # Positive/# Total | Comments | IBV Recovery Outcome |
|---|---|---|---|---|
| 104 | 0 | 0/6 | Healthy embryos | Negative |
| 105 | 0 | 0/6 | " | Negative |
| 110 | 0 | 0/6 | " | Negative |
| 115 | 0 | 0/6 | " | Negative |
| 116 | 0 | 0/6 | " | Negative |
| 118 | 0 | 0/6 | Healthy embryos, except one with no eyes | Negative |
| Uninoculated Eggs | 0 | 0/6 | | Negative |

TABLE 6

VIRUS RECOVERY RECORDS OF NON-VACCINATES: RETESTED SAMPLES

These samples were retested as positive controls for the retested samples in Table 4.
Samples were filtered through 0.45 μm filters before being inoculated into eggs.

| Sample # | # Eggs discarded 3 days post inoculation | # Positive/# Total | Comments | IBV Recovery Outcome |
|---|---|---|---|---|
| 195 | 0 | 5/6 | | Positive |
| 200 | 0 | 5/6 | | Positive |
| 214 | 1 | 4/5 | | Positive |

TABLE 7

VIRUS RECOVERY RECORDS OF VACCINATES: RETESTED SAMPLES

Samples 95, 96, 103, 107, and 119 were retested because of anatomical deformities, not typical for IBV infection, that occurred in embryos during the original test.
Sample 100 was retested to confirm it was negative for virus recovery, because one of six embryos from the original test was smaller than average.
Sample 90 was a retest of a sample that was positive for virus recovery on the original test; it was included as a control.
Sample 124 was a retest of a sample that was negative for virus recovery on the original test; it was included as a control.

| Sample # | # Eggs discarded 3 days post inoculation | # Positive/# Total | Comments | IBV Recovery Outcome |
|---|---|---|---|---|
| 90 | 0 | 3/6 | | Positive |
| 95 | 0 | 0/6 | 1 embryo with open skull; eliminate | Negative |
| 96 | 0 | 0/6; 1 dead | Five embryos are full sized and healthy One dead embryo appears normal-no IBV lesions Discount normal dead per 9CFR 113.327(c)(3)(ii) | Negative |
| 100 | 1 | 0/5 | | Negative |
| 103 | 0 | 0/6 | | Negative |
| 107 | 0 | 1/6 | | Positive |
| 119 | 0 | 2/6 | | Positive |
| 124 | 0 | 0/6 | | Negative |
| Uninoculated Eggs | 0 | 0/6 | | Negative |

We claim:

1. The attenuated GA-98 infectious bronchitis virus deposited at the ATCC under accession no. PTA-4820.

* * * * *